(12) United States Patent
De Stefano et al.

(10) Patent No.: US 11,672,963 B2
(45) Date of Patent: Jun. 13, 2023

(54) DEVICE FOR TRANSDERMAL DELIVERY OF ACTIVE MOLECULES, USES OF THE DEVICE AND METHODS FOR PRODUCING THE DEVICE AND ITS COMPONENTS

(71) Applicant: Altergon SA, Lugano (CH)

(72) Inventors: Luca De Stefano, Naples (IT); Ilaria Rea, Caivano (IT); Principia Dardano, Ercolano (IT); Luigi Nicolais, Ercolano (IT)

(73) Assignee: Altergon SA, Lugano (CH)

( * ) Notice: Subject to any disclaimer, the term of this patent is extended or adjusted under 35 U.S.C. 154(b) by 879 days.

(21) Appl. No.: 16/610,526

(22) PCT Filed: Apr. 6, 2018

(86) PCT No.: PCT/IB2018/052410
§ 371 (c)(1),
(2) Date: Nov. 4, 2019

(87) PCT Pub. No.: WO2018/203156
PCT Pub. Date: Nov. 8, 2018

(65) Prior Publication Data
US 2020/0086102 A1    Mar. 19, 2020

(30) Foreign Application Priority Data
May 4, 2017    (IT) ......................... 102017000048421

(51) Int. Cl.
*A61M 37/00* (2006.01)
*A61K 9/00* (2006.01)
*A61N 5/06* (2006.01)

(52) U.S. Cl.
CPC ....... *A61M 37/0015* (2013.01); *A61K 9/0021* (2013.01); *A61N 5/062* (2013.01);
(Continued)

(58) Field of Classification Search
CPC ...... A61M 37/0015; A61M 2037/0007; A61M 2037/0023; A61M 2037/0061;
(Continued)

(56) References Cited

U.S. PATENT DOCUMENTS

2004/0049150 A1* 3/2004 Dalton .................. A61K 39/00
604/46

* cited by examiner

*Primary Examiner* — Amber R Stiles

(57) ABSTRACT

The object of the present invention is a device (1) for the transdermal delivery of active molecules. The device (1) comprises a support element (8) and a plurality of micro-needles (10) that protrude from a first surface of the support element (8), the support element (8) and the micro-needles (10) being both permeable to the active molecules. The device (1) further comprises a porous membrane (7) configured to be loaded with said active molecules, which lies on a second surface of the support element (8). Characteristically, the porous membrane (7) is configured to behave, from an optical viewpoint, as a Bragg mirror. Further objects of the present invention are the following uses of the device (1): for monitoring the release and/or the decay of the active molecules, for the optical control of the release of the active molecules and for the thermal control of the release of the active molecules. Lastly, an object of the present invention is the method for producing the device (1) for transdermal delivery of active molecules.

18 Claims, 4 Drawing Sheets

(52) U.S. Cl.
CPC ............... *A61M 2037/0007* (2013.01); *A61M 2037/0023* (2013.01); *A61M 2037/0061* (2013.01); *A61N 2005/063* (2013.01); *A61N 2005/0659* (2013.01); *A61N 2005/0662* (2013.01)

(58) Field of Classification Search
CPC .... A61K 9/0021; A61K 9/7023; A61N 5/062; A61N 2005/063; A61N 2005/0659; A61N 2005/0662
See application file for complete search history.

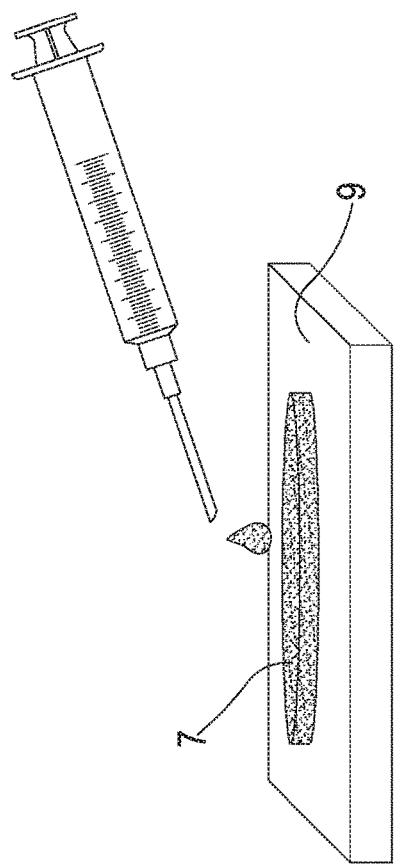
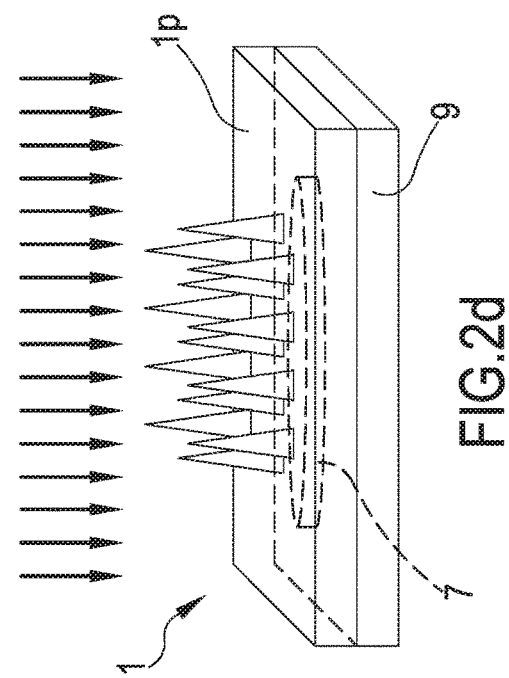
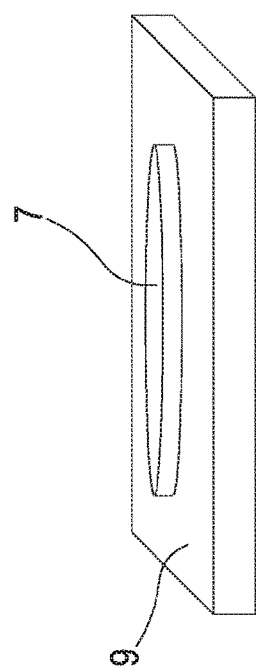
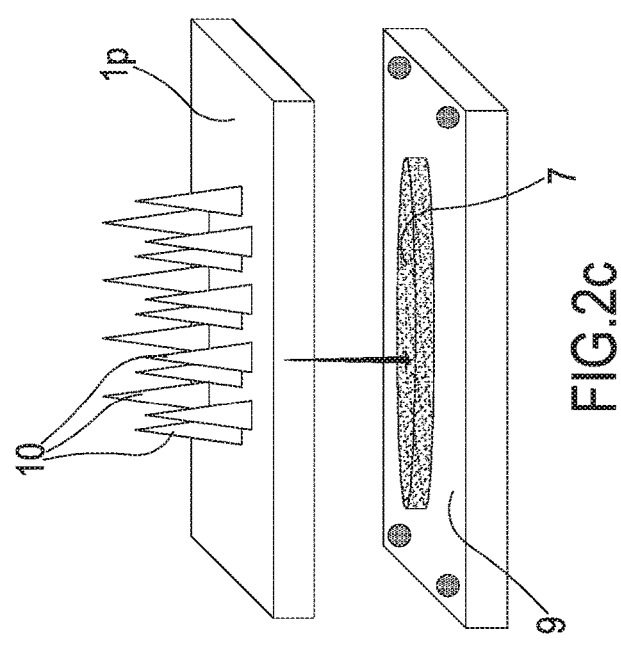

DEVICE FOR TRANSDERMAL DELIVERY OF ACTIVE MOLECULES, USES OF THE DEVICE AND METHODS FOR PRODUCING THE DEVICE AND ITS COMPONENTS

RELATED APPLICATIONS

This application is a National Phase of PCT Patent Application No. PCT/IB2018/052410 having International filing date of Apr. 6, 2018, which claims the benefit of priority of Italian Patent Application No. 102017000048421 filed on May 4, 2017. The contents of the above applications are all incorporated by reference as if fully set forth herein in their entirety.

FIELD AND BACKGROUND OF THE INVENTION

The present invention relates to the technical sector of biomedical devices configured to release active molecules both for topical use and for systemic use. In particular, an object of the present invention is a device for transdermal delivery of active molecules and a method for the production of said device. A further object of the present invention is the use of said device, both for monitoring the release and/or the decay of the active molecules, and for the optical and/or thermal control of the release of the active molecules.

The delivery of drugs transdermal through needles has the drawback of being generally problematic, for example because of the fear of pain, to which is added, for persons suffering from aichmophobia, the fear of the needles themselves. The delivery of drugs through patches or bandages properly functionalised with active biological or synthetic molecules, instead, has the drawback of having quite low efficacy. In the first place, such delivery through patches or bandages is severely hindered by skin, which is a multilayered tissue and acts as a natural barrier against agents external to the human body. Moreover, the manner of release of the drug by the support is purely diffusive, the drug in contact with the skin penetrating by diffusion into the dermis and then into the body. It should also be added that the quantity of active ingredient that can be loaded onto the surface of the tissue is rather limited. Lastly, it should be taken into account that the skin also requires the mixture in contact to be liposoluble, otherwise the hydrophobic effect prevents its permeation.

In recent years, to overcome these drawbacks ever new technological solutions have been developed, both with regard to the materials used in devices for the delivery of drugs, and with regard to the structure of these devices. In particular, the attempt has been made to exploit the microporosity of some support (made of polymeric, plastic or naturally produced materials, like cellulose), to increase the quantity of drugs that can be loaded in the devices and applied on the skin or on an exposed organ. The specific surface area of these supports can be tens or hundreds of times greater than the planar surface (typically, a few square centimetres) of the same supports. Although this technological solution is ameliorative with respect to traditional bandages, nevertheless it completely fails to solve some of the drawbacks mentioned above, in particular the resistance which the corneal layer of the skin exercises against the penetration of the active molecules into the body. A direction of development that has recently been acquiring a great deal of importance is that of miniaturisation, which has enabled the fabrication of micro-needles with variable length from a millimetre to a few hundreds of microns, with such mechanical properties as to be able to indent the first layers of the dermis without reaching the layer where nerves are present and hence completely eliminating the painful sensation tied to the penetration of the needles.

Micro-needles, thanks to their flexibility that makes them particularly suitable for innovative applications in the biomedical field, are currently the subject of clinical studies to allow the release, through them, of active molecules such as vaccines (for example, the flu vaccine), insulin, parathyroid hormone. These clinical studies, moreover, are highlighting the potential which micro-needles can have in theranostics as well. It has been ascertained that micro-needles allow an optimal exchange of active molecules between the exterior of the human body and the interstitial fluid under the corneal layer, this layer being the first layer of skin that is practically impermeable to all molecules with molecular weight above 500 Dalton. Micro-needles thus allow the transdermal delivery of active molecules even of high molecular weight, for example of biomolecules such as proteins or antibodies that can reach a weight of hundreds of kDa, therefore providing an alternative to the oral or systemic delivery of active molecules.

Moreover, micro-needles are also very promising in consideration of their possible uses in diagnostics. Once the barrier of epithelial tissue is pierced by the tip of a micro-needle, a channel is in fact created, through which it is possible to continuously monitor glucose, lactate, pH and other substances with minimal risk and minimal invasiveness. Many examples of biomedical devices adapted to release active molecules and provided with micro-needles are known from the patent literature, for example from the patent documents WO2016/142705A1, WO2016/155891 A1, CN105641801A, WO2016/145299A1, US2011/0237925A1, US2012/0123341A1 and WO2013/165715A1. The devices illustrated in these documents are heterogeneous, but none of them is free of critical issues in relation to the production process and/or to the structure and/or the constituent materials (both inorganic materials such as silicon, glass, mixed oxides, and organic materials such as polymers, plastics, cellulose).

The document US2013/0150822A1 discloses a technical solution for increasing the permeability of drugs into the skin by means of a device comprising nanostructures arranged according to a predetermined pattern on the face of the device that is intended to come in contact with the patient's skin. The device is embodied in the form of a transdermal patch comprising a reservoir into which the drug is loaded; a membrane that serves as a control membrane, slowing down the rate of release of the drug; a removable layer that inhibits the release of the drug until said layer is removed and a plurality of micro-needles that penetrate the patient's skin.

The document US2007/0060867A1 discloses a device for transdermal delivery of active substances in a controlled manner. The device comprises an array of microstructures having an aspect ratio equal to or greater than 10:1.

The document U.S. Pat. No. 3,964,482 discloses a device for the transdermal delivery of a drug, comprising a reservoir containing the drug and a plurality of projections protruding from a wall of the reservoir. The projections are shaped as needles, to be capable of penetrating the stratum corneum of the skin.

The document CN102553066B discloses a system for the transdermal delivery of a drug. The system comprises porous microneedles that are developed starting from a polymeric film and that are connected, by means of a pump, to a reservoir for feeding the drug. A purpose of the present invention is to provide a device adapted to release active molecules and provided with microneedles that is able to assure an optimal delivery of the active molecules.

SUMMARY OF THE INVENTION

A purpose of the present invention is to provide a device adapted to release active molecules that is effectively adaptable to the specifity of each drug or vaccine with regard to dosage, time of release and release mode and whose production method allows changes to be made easily and quickly to the shape, the length and the mechanical properties of the micro-needles.

A purpose of the present invention is to provide a device adapted to release active molecules distinguished by considerable versatility and therefore suitable to be used for multiple applications, both therapeutic and diagnostic. A purpose of the present invention is to provide a device adapted to release active molecules that is arranged for large scale industrial production at very low costs and whose production method assures optimal repeatability and optimal precision, with extremely small tolerances in the dimensions of the components.

A purpose of the present invention is to provide a device adapted to release active molecules that is biocompatible so that, when in contact with the skin, it causes no irritations or infections and that is sufficiently strong and flexible to adapt to any point of application on the human body.

A purpose of the present invention is to provide a device adapted to release active molecules that can be integrated in control networks and that can interface with electronic control devices.

A purpose of the present invention is to provide a device adapted to release active molecules that is arranged for utilisation modes in which the release of the active molecules can be monitored (passive control) and/or modulated (active control).

All purposes are fully achieved by the present invention, which includes the aspects listed below.

A first aspect of the invention relates to a device (1) for the transdermal delivery of active molecules, comprising:
  a support element (8) permeable to said active molecules;
  a plurality of micro-needles (10) permeable to said active molecules, said micro-needles (10) protruding from a first surface (8p) of said support element (8) and
  a porous membrane (7) configured to be loaded with said active molecules, said porous membrane (7) lying on a second surface (8s) of said support element (8), said second surface (8s) being preferably the surface of said support element (8) opposite to said first surface (8p); wherein, according to the invention, said porous membrane (7) is configured to behave, from an optical viewpoint, as a Bragg mirror or as a linear combination between Bragg mirrors, possibly interspersed with one or more flaws so as to generate single or coupled optical cavities.

A second aspect of the invention, dependent on the first aspect, relates to a device (1) for the transdermal delivery of active molecules, wherein said micro-needles (10) are obtained with photolithographic or micromechanical techniques.

A third aspect of the invention, dependent on the first aspect or on the second aspect, relates to a device (1) for the transdermal delivery of active molecules, wherein said micro-needles (10) constitute a single body with said support element (8). A fourth aspect of the invention, dependent on any of the preceding aspects, relates to a device (1) for the transdermal delivery of active molecules, wherein said micro-needles (10) and/or said support element (8) are based on at least one photoresistant hybrid polymeric mixture, optionally a photoresistant mixtured based on PolyEthylene (Glycol) DiAcrylate (PEGDA) and on a photocatalyst, optionally 2-Hydroxy-2-methyl-1-phenyl-propan-1-one (Darocur®), in particular said photoresist mixture having a concentration of 2-Hydroxy-2-methyl-1-phenyl-propan-1-one (Darocur®)) in PolyEthylene (Glycol) DiAcrylate (PEGDA) of approximately 2% volume/volume.

A fifth aspect of the invention, dependent on any of the preceding aspects, relates to a device (1) for the transdermal delivery of active molecules, wherein said porous membrane (7) is porous silicon (PSi) based and it is optionally oxidised in an ethanol bath, said porous membrane (7) being preferably obtained by means of an electrochemical process, in particular by electrochemical dissolution of crystalline silicon with p++ doping in a solution of hydrofluoric acid, water and ethanol, hydrofluoric acid (HF), water and ethanol being in a ratio of approximately 1:1:1 in said solution.

A sixth aspect of the invention, dependent on any of the preceding aspects, relates to a device (1) for the transdermal delivery of active molecules, wherein the number of periods in said porous membrane (7) is between 10 and 50, preferably between 20 and 40, yet more preferably equal to 30. A seventh aspect of the invention, dependent on any of the preceding aspects, relates to a device (1) for the transdermal delivery of active molecules, said micro-needles (10) extending from a first portion of said support element (8) and said porous membrane (7) contacting a second portion of said support element (8), wherein said first portion is internal to said second portion, so that said active molecules can diffuse from said porous membrane (7) in said support element (8) and thence in said micro-needles (10). An eighth aspect of the invention, dependent on any of the preceding aspects, relates to a device (1) for the transdermal delivery of active molecules, wherein a closing element (9) is connected to said second surface (8s) of said support element (8), said closing element (9) adhering peripherally to said support element (8) so that said porous membrane (7) is sealed between said closing element (9) and said support element (8), said closing element (9) preferably being made of the same material as said support element and/or based on at least one photoresistant hybrid polymeric mixture, optionally a photoresistant mixture based on PolyEthylene (Glycol) DiAcrylate (PEGDA) and on a photocatalyst, optionally 2-Hydroxy-2-methyl-1-phenyl-propan-1-one (Darocur®), in particular said photoresistant mixture presenting a concentration of 2-Hydroxy-2-methyl-1-phenyl-propan-1-one (Darocur®)) in PolyEthylene (Glycol) DiAcrylate (PEGDA) of approximately 2% volume/volume.

A ninth aspect of the invention, dependent on any of the preceding aspects, relates to a device (1) for the transdermal delivery of active molecules, wherein said porous membrane (7) comprises a porous matrix having high specific surface area with resonant photonic structure, said porous membrane (7) comprising layers with different porosity.

A tenth aspect of the invention, dependent on any of the preceding aspects, relates to a device (1) for the transdermal delivery of active molecules, wherein said support element (8) and/or said micro-needles (10) and/or said porous membrane (7) have morphological and surface chemical characteristics to modulate the release of said active molecules over time according to predetermined time intervals and/or according to the hydrophobic and/or hydrophilic nature of said active molecules.

An eleventh aspect of the invention, dependent on any of the preceding aspects, relates to a device (1) for the transdermal delivery of active molecules, said device (1) being flexible. A twelfth aspect of the invention, dependent on any of the preceding aspects, relates to a device (1) for the transdermal delivery of active molecules, wherein the extension of said micro-needles (10) is between 0.1 mm and 2 mm, preferably between 0.4 mm and 1.5 mm, still more preferably between 0.7 mm and 0.9 mm and/or wherein the thickness of said support element (8) is between 0.3 mm and 1.8 mm, preferably between 0.7 and 1.3 mm, still more preferably between 0.9 mm and 1.1 mm, the thickness of said closing element (9) being in particular between 0.2 mm and 1.2 mm, preferably between 0.3 mm and 0.9 mm, still more preferably between 0.4 mm and 0.6 mm and/or wherein said porous membrane (7) is configured to be further loaded with carrier molecules, said carrier molecules being suitable to carry said active molecules, said carrier molecules comprising in particular molecules of bovine serum albumin (BSA).

A thirteenth aspect of the invention, dependent on any of the preceding aspects, relates to a device (1) for the transdermal delivery of active molecules, said active molecules comprising molecules of at least one fluorescent substance, in particular fluorescein ($C_{20}H_{12}O_5$), the colour of said fluorescent substance veering as a result of a change of at least one representative parameter of said fluorescent substance in said porous membrane (7), wherein said porous membrane (7) is in particular configured to have at least one transmissivity window in the spectrum of visible light, said transmissivity window including within it the range of wavelengths of the radiation emitted by said fluorescent substance when said at least one parameter is within a predefined range. A fourteenth aspect of the invention, dependent on the thirteenth aspect, relates to a device (1) for the transdermal delivery of active molecules, said parameter comprising the concentration of said fluorescent substance in said porous membrane (7) and/or the state of oxidation and/or of decay of said fluorescent substance in said porous membrane (7), wherein said porous membrane (7) is in particular configured to have:

at least a first transmissivity window in the spectrum of visible light, said first transmissivity window including within it the range of wavelengths of the radiation emitted by said fluorescent substance when the concentration of said fluorescent substance in said porous membrane (7) is high, typically as a result of the charging of said fluorescent substance in said porous membrane (7) and/or at least a second transmissivity window in the spectrum of visible light, said second transmissivity window including within it the range of wavelengths of the radiation emitted by said fluorescent substance when the concentration of said fluorescent substance in said porous membrane (7) is low, typically as a result of the release of said fluorescent substance by said porous membrane (7) and/or at least a third transmissivity window in the spectrum of visible light, said third transmissivity window including within it the range of wavelengths of the radiation emitted by said fluorescent substance when said fluorescent substance in said porous membrane (7) is substantially decayed, typically as a result of the oxidation over time of said fluorescent substance in said porous membrane (7); said first, second and third transmissivity windows being separate from each other and optionally corresponding to distinct colours.

A fifteenth aspect of the invention, dependent on any of the preceding aspects, relates to a device (1) for the transdermal delivery of active molecules, said active molecules comprising molecules of at least one photoresponsive substance, wherein said porous membrane (7) is configured to have at least one transmissivity window and is suitable to allow a radiation to which said porous membrane (7) is exposed to traverse said porous membrane (7) only if the wavelength of said radiation coincides with said transmissivity window or is included in said transmissivity window.

A sixteenth aspect of the invention, dependent on the fifteenth aspect, relates to a device (1) for the transdermal delivery of active molecules, wherein said transmissivity window is in the infrared spectrum, in particular in the near infrared spectrum.

A seventeenth aspect of the invention, dependent on the fifteenth aspect or on the sixteenth aspect, relates to a device (1) for the transdermal delivery of active molecules, wherein said photoresponsive substance comprises a photoresponsive polymer or hydrogel, optionally a photoresponsive derivative or ester of acrylic acid or of polyvinyl alcohol or of polymethacrylate or of hyaluronic acid or of polyethylene glycol. An eighteenth aspect of the invention, dependent on any of the preceding aspects, relates to a device (1) for the transdermal delivery of active molecules, said active molecules comprising molecules and/or particles of at least one thermoresponsive substance, said thermoresponsive substance activating when subjected to a predetermined temperature increase for a predetermined duration.

A nineteenth aspect of the invention, dependent on the eighteenth aspect, relates to a device (1) for the transdermal delivery of active molecules, said active molecules comprising molecules and/or particles of a first thermoresponsive substance and molecules and/or particles of a second thermoresponsive substance, said first thermoresponsive substance comprising nanoparticles of a non-noble metal, optionally iron, which in the presence of oxygen and of a catalyst, optionally graphene, change oxidation state with an exothermic reaction, said second thermoresponsive substance comprising gold nanoparticles obtained by reduction of a gold salt in the presence of a reducing compound, optionally sodium borohydride, said gold nanoparticles being in particular spherical with diameter between 5 and 100 nm or cylindrical with minor axis smaller than 10 nm and major axis up to 100 nm.

A twentieth aspect of the invention relates to a use of a device (1) for the transdermal delivery of active molecules, said device (1) comprising:

a support element (8) permeable to said active molecules;—a plurality of micro-needles (10) permeable to said active molecules, said micro-needles (10) protruding from a first surface (8p) of said support element (8);

a porous membrane (7) loaded with said active molecules, said porous membrane (7) lying on a second surface (8s) of said support element (8), said second surface (8s) being preferably the surface of said support element (8) opposite to said first surface (8p); said active molecules comprising molecules of at least one fluorescent substance, in particular fluoroscein ($C_{20}H_{12}O_5$), said porous membrane (7) being configured to behave, from an optical viewpoint, as a Bragg mirror or as a linear combination between Bragg mirrors or as a single or coupled optical cavity, the colour of said fluorescent substance veering as a result of a change of at least one representative parameter of said active molecules and/or of said fluorescent substance in said porous membrane (7), said parameter comprising in particular the concentration of said active molecules and/or of said fluorescent substance in said porous membrane (7) and/or the state of oxidation and/or of decay of said active molecules and/or of said fluorescent substance in said porous membrane (7), for monitoring the release and/or the decay of said active molecules.

A twenty-first aspect of the invention relates to a use of a device (1) for the transdermal delivery of active molecules, said device (1) comprising:

a support element (8) permeable to said active molecules;
a plurality of micro-needles (10) permeable to said active molecules, said micro-needles (10) protruding from a first surface (8p) of said support element (8);
a porous membrane (7) loaded with said active molecules, said porous membrane (7) lying on a second surface (8s) of said support element (8), said second surface (8s) being preferably the surface of said support element (8) opposite to said first surface (8p); said active molecules comprising molecules of at least one photoresponsive substance, said photoresponsive substance comprising in particular a photoresponsive polymer or hydrogel, optionally a photoresponsive derivative or ester of acrylic acid or of polyvinyl alcohol or of polymethacrylate or of hyaluronic acid or of polyethylene glycol, said porous membrane (7) being configured to behave, from an optical viewpoint, as a Bragg mirror or as a linear combination between Bragg mirrors or as a single or coupled optical cavity, and to have at least one transmissivity window, optionally in the infrared spectrum, in particular in the near infrared spectrum. for the optical control of the release of said active molecules, the release of said active molecules being able to take place only in a condition of exposure of said device (1) to a radiation having a wavelength coinciding with said transmissivity window or included in said transmissivity window.

A twenty-second aspect of the invention relates to a use of a device (1) for the transdermal delivery of active molecules, said device (1) comprising:

a support element (8) permeable to said active molecules;
a plurality of micro-needles (10) permeable to said active molecules, said micro-needles (10) protruding from a first surface (8p) of said support element (8);
a porous membrane (7) loaded with said active molecules, said porous membrane (7) lying on a second surface (8s) of said support element (8), said second surface (8s) preferably being the surface of said support element (8) opposite to said first surface (8p), said active molecules comprising molecules and/or particles of at least one thermoresponsive substance, said thermoresponsive substance activating when subjected to a predetermined temperature increase for a predetermined duration, said thermoresponsive substance comprising in particular nanoparticles of a non-noble metal, optionally iron, and a catalyst, optionally graphene, and/or gold nanoparticles, for the thermal control of the release of said active molecules, the release of said active molecules being able to take place only under thermal activation condition, in particular as a result of a change of the state of oxidation of said active molecules and/or as a result of the irradiation of said active molecules.

A twenty-third aspect of the invention relates to a method for producing a component (1 p) for a device (1) for the transdermal delivery of active molecules, comprising the step of obtaining a plurality of micro-needles (10) on a surface of a support element (8) with photolithographic or micromechanical techniques. A twenty-fourth aspect of the invention, dependent on the twenty-third aspect, relates to a method for producing a component (1 p) for a device (1) for the transdermal delivery of active molecules, wherein said support element (8) is obtained depositing a photoresistant hybrid polymeric mixture on a substrate (5) and then hardening said photoresistant mixture by exposure to a source of ultraviolet radiation, preferably for a duration of approximately 10 seconds, said photoresistant mixture optionally being based on PolyEthylene (Glycol) DiAcrylate (PEGDA) and on a photocatalyst, optionally 2-Hydroxy-2-methyl-1-phenyl-propan-1-one (Darocur®), in particular said photoresistant mixture having a concentration of 2-Hydroxy-2-methyl-1-phenyl-propan-1-one Darocur®) in PolyEthylene (Glycol) DiAcrylate (PEGDA) of approximately 2% volume/volume.

A twenty-fifth aspect of the invention, dependent on the twenty-fourth aspect, relates to a methof for producing a component (1p) for a device (1) for the transdermal delivery of active molecules, wherein said substrate (5) is made of a material that is transparent to ultraviolet radiation, in particular quartz.

A twenty-sixth aspect of the invention, dependent on any aspect from the twenty-third aspect to the twenty-fifth aspect, relates to a method for producing a component (1p) for a device (1) for the transdermal delivery of active molecules, wherein the micro-needles (10) are obtained hardening, by exposure to a source of ultraviolet radiation, at least one photoresistant hybrid polymeric mixture, optionally said photoresistant mixture being the same photoresistant mixture used as starting material for making said support element (8) and/or being based on PolyEthylene (Glycol) DiAcrylate (PEGDA) and on a photocatalyst, optionally 2-Hydroxy-2-methyl-1-phenyl-propan-1-one (Darocur®)), in particular said photoresistant mixture presenting a concentration of 2-Hydroxy-2-methyl-1-phenyl-propan-1-one (Darocur®)) in PolyEthylene (Glycol) DiAcrylate (PEGDA) of approximately 2% volume/volume.

A twenty-seventh aspect of the invention, dependent on the twenty-sixth aspect, relates to a method for producing a component (1 p) for a device (1) for the transdermal delivery of active molecules, wherein said photoresistant mixture is contained in a container (4), preferably made of silicone, said support element (8) bearing on said container (4) so as to be in direct contact with said photoresistant mixture.

A twenty-eighth aspect of the invention, dependent on the twenty-sixth aspect or on the twenty-seventh aspect, relates to a method for producing a component (1 p) for a device (1) for the transdermal delivery of active molecules, wherein a mask (2) impermeable to ultraviolet radiation is interposed between said source of ultraviolet radiation and said support element (8), said mask having a plurality of openings at the points of application of said micro-needles (10) on said support element (8).

A twenty-ninth aspect of the invention, dependent on any aspect from the twenty-sixth aspect to the twenty-eighth aspect, relates to a method for producing a component (1 p) for a device (1) for the transdermal delivery of active molecules, wherein, after photolithography, said micro-needles (10) are subjected first to a washing step, optionally in deionized water and/or for approximately 2 minutes, to remove the unhardened photoresistant mixture, and then to a drying step, optionally with nitrogen.

A thirtieth aspect of the invention, dependent on any aspect from the twenty-sixth aspect to the twenty-ninth aspect, relates to a method for producing a component (1p) for a device (1) for the transdermal delivery of active molecules, wherein, after photolithography, said support element (8) is subjected to a cutting step, in particular to remove said substrate (5) from said support element (8).

A thirty-first aspect of the invention relates to a method for producing a porous membrane (7) for a device (1) for the transdermal delivery of active molecules, comprising the step of configuring said porous membrane (7) to behave, from an optical viewpoint, as a Bragg mirror or as a linear combination between Bragg mirrors or as a single or coupled optical cavity.

A thirty-second aspect of the invention, dependent on the thirty-first aspect, relates to a method for producing a porous membrane (7) for a device (1) for the transdermal delivery of active molecules, comprising the step of making a porous matrix having high specific surface area with resonant photonic structure.

A thirty-third aspect of the invention, dependent on the thirty-first aspect or on the thirty-second aspect, relates to a method for producing a porous membrane (7) for a device (1) for the transdermal delivery of active molecules, comprising the step of making said porous membrane (7) by superposing layers with different porosity.

A thirty-fourth aspect of the invention, dependent on the thirty-third aspect, relates to a method for producing a porous membrane (7) for a device (1) for the transdermal delivery of active molecules, said superposition of layers providing the alternation between a lower porosity layer and a higher porosity layer. A thirty-fifth aspect of the invention, dependent on any aspect from the thirty-first aspect to the thirty-fourth aspect, relates to a method for producing a porous membrane (7) for a device (1) for the transdermal delivery of active molecules, wherein the number of periods in said porous membrane (7) is between 10 and 50, preferably between 20 and 40, still more preferably equal to 30.

A thirty-sixth aspect of the invention, dependent on any aspect from the thirty-first aspect to the thirty-fifth aspect, relates to a method for producing a porous membrane (7) for a device (1) for the transdermal delivery of active molecules, wherein said porous membrane (7) is obtained by means of an electrochemical process.

A thirty-seventh aspect of the invention, dependent on the thirty-sixth aspect, relates to a method for producing a porous membrane (7) for a device (1) for the transdermal delivery of active molecules, wherein said porous membrane (7) is porous silicon (PSi) based and is optionally obtained by electrochemical dissolution of crystalline silicon with p++ doping in a solution of hydrofluoric acid (HF), water and ethanol, hydrofluoric acid (HF), water and ethanol being in a ratio of approximately 1:1:1 in said solution.

A thirty-eighth aspect of the invention, dependent on any aspect from the thirty-first aspect to the thirty-seventh aspect, relates to a method for producing a porous membrane (7) for a device (1) for the transdermal delivery of active molecules, wherein said porous membrane (7) is loaded with active molecules.

A thirty-ninth aspect of the invention, dependent on the thirty-eighth aspect, relates to a method for producing a porous membrane (7) for a device (1) for the transdermal delivery of active molecules, wherein said active molecules comprise molecules of at least one fluorescent substance, in particular fluorescein (C20H1205), and/or molecules of at least one photoresponsive substance, in particular a photoresponsive polymer or hydrogel, optionally a photoresponsive derivative or ester of acrylic acid or of polyvinyl alcohol or of polymethacrylate or of hyaluronic acid or of polyethylene glycol and/or molecules and/or particles of at least one thermoresponsive substance, said thermoresponsive substance comprising in particular nanoparticles of a non-noble metal, optionally iron, and a catalyst, optionally graphene, and/or gold nanoparticles.

A fortieth aspect of the invention, dependent on the thirty-eighth aspect or on the thirty-ninth aspect, relates to a method for producing a porous membrane (7) for a device (1) for the transdermal delivery of active molecules, wherein said porous membrane (7) is dried before being loaded with said active molecules.

A forty-first aspect of the invention relates to a method for producing a device (1) for the transdermal delivery of active molecules, comprising the steps of assembling a component (1 p) obtained with the production method according to any of the aspects from the twenty-third aspect to the thirtieth aspect to a porous membrane (7) obtained with the production method according to any of the aspects from the thirty-first aspect to the fortieth aspect.

A forty-second aspect of the invention, dependent on the forty-first aspect, relates to a method for producing a device (1) for the transdermal delivery of active molecules, wherein the assembly between said component (1 p) and said porous membrane (7) takes place by means of a closing element (9).

A forty-third aspect of the invention, dependent on the forty-second aspect, relates to a method for producing a device (1) for the transdermal delivery of active molecules, wherein said porous membrane (7) is deposited on said closing element (9) and said closing element (9) is connected to a surface of said support element (8) so as to make said closing element (9) adhere peripherally to said support element (8) and consequently to seal said porous membrane (7) between said closing element (9) and said support element (8), the surface of said support element (8) to which said closing element (9) is connected being in particular the opposite surface to the one on which said micro-needles (10) are applied.

A forty-fourth aspect of the invention, dependent on the forty-third aspect, relates to a method for producing a device (1) for the transdermal delivery of active molecules, wherein said closing element (9) is connected to a surface of said support element (8) by the application of a photoresistant liquid and by hardening said photoresistant liquid by means of an ultraviolet radiation. A forty-fifth aspect of the invention, dependent on the forty-third aspect, relates to a method for producing a device (1) for the transdermal delivery of active molecules, wherein said closing element (9) is connected to a surface of said support element (8) by the application of a glue.

BRIEF DESCRIPTION OF THE SEVERAL VIEWS OF THE DRAWINGS

The inventive features of the aspects listed below will be more readily apparent from the following detailed description, in which reference will be made to the following figures in which.

Figures from FIG. 1 *a* to FIG. 1*f* represent, through a series of section views, the steps of the method for producing a component of a device for the transdermal delivery of active molecules according to the present invention.

Figures from FIG. 2*a* to FIG. 2*d* represent, in schematic form, through a series of axonometric view, the steps of the method for producing a device for the transdermal delivery of active molecules according to the present invention

DESCRIPTION OF SPECIFIC EMBODIMENTS OF THE INVENTION

Figure 1A:
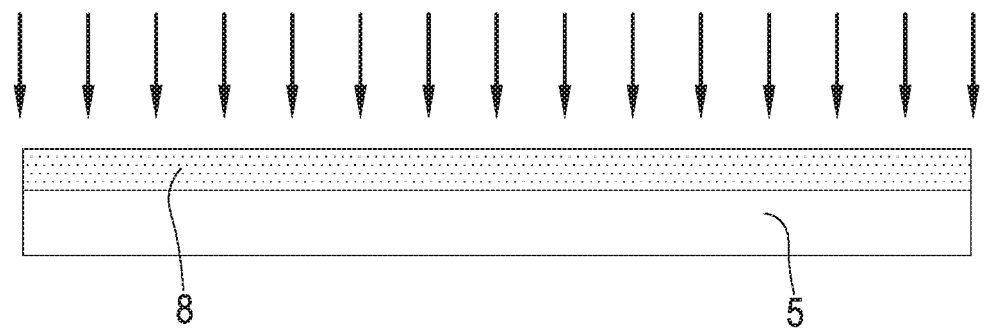

FIG. 2*d* represents a device 1 for the transdermal delivery of active molecules according to the present invention. The device is shown in FIG. 2*d* in schematic form and not to scale. The device 1 is of a hybrid type, because it consists partly of organic materials and partly of inorganic materials. The device 1 is configured to be applied directly on human skin. For this purpose, it has adequate characteristics of elasticity, so it is able to flex significantly without breaking and consequently it can be applied to any part of the human body surface. From a geometric viewpoint, it has a fundamentally two-dimensional development (with very small thickness) and it has an extension of a few square centimetres. Moreover, it is distinguished by particular optical properties, which will be described in detail below. The device 1 allows the transdermal delivery of active molecules (for example drugs or vaccines) in an easy, substantially painless and particularly effective way. In particular, through the device 1, hydrophilic molecules and/or molecules with high molecular weight can also be delivered (which cannot be delivered with the traditional patches and bandages).

For the delivery of the active molecules, the device 1 comprises a plurality of micro-needles 10, which have a very small length (so as not to reach nerve terminations and therefore not to cause pain to the person), but still greater than the thickness of the corneal layer of the skin, so that the delivery of the active molecules is possible even when the active molecules are hydrophilic and/or have high molecular weight. Each of the micro-needles 10, when the device 1 is applied to the skin, causes a (reversible) micro-rupture of the corneal layer and therefore creates a micro-channel that the active molecules can then traverse, overcoming the obstacle to their penetration in the body, constituted by the corneal layer, and thus reaching the interstitial liquid.

To perform their function correctly, the micro-needles 10 are made of a material that is permeable to the active molecules. In particular, the micro-needles 10 are made of a polymeric material, preferably with photolithographic techniques (by means of the method whose steps will be described in detail below). Photolithography makes it possible define very precisely the geometry of the micro-needles 10 and very easily to make any shape adaptation directed at modifying this geometry. Moreover, photolithography is particularly indicated for large scale production of the microneedles 10, requiring very low costs. Alternatively to photolithography, the micro-needles 10 can be obtained with micromechanical techniques.

To allow their realisation by means of photolithography, the micro-needles 10 are made starting from a photoresistant hybrid polymeric mixture, optionally a photoresistant mixture based on PolyEthylene (Glycol) DiAcrylate (PEGDA) and on a photocatalyst, optionally 2-Hydroxy-2-methyl-1-phenyl-propan-1-one (Darocur®), in particular said photoresistant mixture presenting a concentration of Darocur® in PEDGA of approximately 2% volume/volume. PEDGA is particular apt to be employed for the realisation of the micro-needles 10, in particular by virtue of the biocompatibility, biodegradability, resilience and strength of this material. Alternatively to PEGDA, other suitable material for the realisation of the micro-needles 10 are polymethacrylate, lactic polyacid, glycolic polyacid, glycolic lactic polyacid, cyclic olefin copolymers, polyvinylpyrrolidone, sodium carboxymethy lcellulose and carbohydrates like galactose, maltose and dextrins.

From a geometric viewpoint, the micro-needles 10 are micro-projections that protrude from a surface 8*p* of a support element 8, advantageously constituting a single body with said support element 8. The micro-needles 10 protrude from the surface 8*p* of the support element 8 remaining substantially parallel to each other. Advantageously, the microneedles 10 extend along a substantially orthogonal direction to the surface 8*p*. The extension of the micro-needles 10 is between 0.1 mm and 2 mm, preferably between 0.4 mm and 1.5 mm, still more preferably between 0.7 mm and 0.9 mm. The micro-needles 10 are densely arranged on the surface 8*p* of the support element 8 from which they protrude, the distance between two consecutive micro-needles being of the order of a few tens of millimetres. The micro-needles 10 are bodies with conical, pyramidal or cylindrical shape with circular or polygonal cross section. Advantageously, the micro-needles 10 terminate with a tapered end so that a tip is obtained for rupturing the corneal layer and the transdermal penetration of the micro-needles 10 through to the interstitial liquid.

The support element 8, especially when in a single body with the micro-needles 10, is also advantageously obtained through photolithographic techniques starting from a photoresistant hybrid polymeric mixture, for example a photoresistant mixture based on PEGDA and on a photocatalyst, optionally Darocur®, in particular this photoresistant mixture having a concentration of Darocur® in PEGDA of approximately 2% volume/volume. The support element 8 has a substantially planar configuration when the device 1 is not subjected to deformations, the thickness of the support element 8 being of the order of some tens of a millimetre, for example between 0.3 mm and 1.8 mm, preferably 0.7 mm and 1.3 mm, still more preferably between 0.9 mm and 1.1 mm. However, the elasticity of PEGDA provides the support element 8 with an ample ability to flex, so that the support element 8 can, when in use, adapt to the conformation of the part of the human body surface on which the device 1 is applied. Moreover, PEGDA has adequate porosity so that the active molecules can diffuse at first through the support element 8 and then through the micro-needles 10 and can then be released by the device 1.

In addition to the component that includes the support element 8 and the micro-needles 10, an additional specific component of the device 1 is a porous membrane 7 configured to be loaded with the active molecules. The porous membrane 7 is self-supporting (so it has a stable volume) and lies on a surface of the support element 8, preferably on the surface 8*s* of the support element 8 opposite to the surface 8*p* from which the micro-needles 10 protrude. Since the porous membrane 7 directly contacts the surface 8*s* of the support element 8, the active molecules move from the porous membrane 7 towards the support element 8 and, because of the characteristics of the polymeric material whereof the support element 8 is made, diffuse in the support element 8 and in the micro-needles 10, until reaching a condition of physical equilibrium. To optimise the diffusive processes within the device 1, the porous membrane 7 is positioned as close to the micro-needles 10 as possible. Advantageously, assuming as a reference the portion of the support element 8 from which the micro-needles 10 develop, this portion is internal to the portion (moderately more extended) of the support element that is contacted by the porous membrane 7. Advantageously, the porous membrane 7 comprises a porous membrane (in combination with a high specific surface), so as to be adequately loaded with active molecules and therefore to serve as a reservoir, in which to accumulate a significant quantity of active molecules progressively releasable by a diffusive process through the support element 8 and the micro-needles 10. A suitable material for the realisation of the porous membrane 7 is porous silicon (PSi), the porous membrane 7 being optionally oxidised in an ethanol bath. Advantageously, the porous membrane 7 is obtained by an electrochemical process. A suitable electrochemical process is a process of electrochemical dissolution of crystalline silicon with p++ doping in a solution of hydrofluoric acid (HF), water and ethanol, hydrofluoric acid (HF), water and ethanol being in a ratio of approximately 1:1:1 in this solution.

The porous membrane 7 is properly sealed within the device 1 so as to prevent the porous membrane 7 from losing the correct interfacing with the support element 8 and/or even a small part of the quantity of active molecules loaded in the porous membrane 7 from being dispersed, in the absence of intentional diffusive processes through the micro-needles 10. For this purpose, the device 1 comprises a closing element 9 that adheres peripherally and stably to the support element 8, so that the porous membrane 7 is in fact deprived of any possibility to move. Advantageously, the closing element 9 is made of the same material as the support element 8: the two elements thus have identical elasticity, hence avoiding, when the device 1 is deformed (for example subject to bending, being applied to a curved area of the human body surface), the emergence of tensions between the elements that can cause a breakage of the device 1.

The closing element 9 can be based on at least one photoresistant hybrid polymeric mixture, optionally a photoresistant mixture based on PEGDA and a photocatalyst, optionally Darocur®, in particular said photoresistant mixture having a concentration of Darocur® in PEGDA of approximately 2% volume/volume. Alternatively, the closing element 9 can be made of quartz. The closing element 9 advantageously has substantially shape identity with the support element 8, and hence has substantially planar configuration when the device 1 is not subject to deformations. The thickness of the closing element 9 can be comparable to the thickness of the support element 8, or even suitably lower (e.g., approximately half of the thickness of the support element 8). The thickness of the closing element 9 can be between 0.2 mm and 1.2 mm, preferably between 0.3 mm and 0.9 mm, still more preferably between 0.4 mm and 0.6 mm.

The connection between the support element 8 and the closing element 9 is intentionally irreversible, because any disconnection between the two elements would free the porous membrane 7 and therefore would definitively damage the device 1. In a first embodiment of the present invention, the support element 8 is connected to the closing element 9 by means of a hardened photoresistant mixture, advantageously by means of a mixture having the same composition of the material of which the support element 8 and/or the closing element 9 are made (thus for example by means of a photoresistant mixture, specifically based on PEGDA and on a photocatalyst, Darocur® being usable as photocatalyst). In a second embodiment of the present invention, the support element 8 is connected to the closing element 9 by means of the application of a glue between the support element 8 and the closing element 9.

In addition to the storage properties, the present invention also employs the optical properties of the porous membrane 7, given that the porous matrix constituting the porous membrane 7 has a resonant photonic structure, in which layers with different porosity alternate. Such a structure enables the porous membrane 7 to behave, from an optical viewpoint, as a Bragg mirror or as a linear combination between Bragg mirrors or as a single or coupled optical cavity and consequently to implement in the device 1 both a passive control, and an active control of the release of the active molecules, said controls being based on the optical properties of the porous membrane 7.

It should be recalled that the expression "Bragg mirror' (sometimes called "Bragg grating") refers, in the sector of optics, to an element in which layers of material with different refractive index alternate, so that said element is able to filter particular wavelengths.

A Bragg mirror has a periodic structure with the alternation of layers with low refractive index ($n_i$_) and layers with high refractive index (ПH). The refractive index n of a layer is correlated with the porosity P of that layer and in particular it decreases as the porosity P increases. The thicknesses $d_i$_and dH of the layer follow the relationship Image available on "Original document" where m is a constant of the material (correlated with diffraction phenomena) and AB is the wavelength filtered by the Bragg mirror. A Bragg mirror is usually indicated with $[n_i\_n_H]N$, where N is the number of periods.

The product between the refractive index n of a layer and the thickness d of that layer is commonly called "optical path" (or alternatively "optical thickness"). The optical features of the porous membrane 7 can be modulated by changing porosity (and hence the value of the refractive index n) and thickness d so that the optical thickness nd assumes such values as to induce the presence of particular optical resonances in the spectrum of reflection and/or transmission of the porous membrane 7. Changing the order of the layers of porous silicon and the respective values of optical path nd for each layer, it is then possible to obtain single or coupled optical cavities (i.e. optical structures that have a transmissivity peak in a high reflectivity region), where the expression "coupled optical cavities" means high reflectivity regions with two or more transmissivity peaks that comprehensively form, from the optical viewpoint, a linear combination between Bragg mirrors. From a structural viewpoint, coupled optical cavities are obtained by means of a sequence of Bragg mirrors interspersed by layers distinguished by a relatively low refractive index or by a relatively high refractive index, said layers being defined "flaws". In the particular case of a sequence between a first Bragg mirro having an optical path $[n_id_i]N_i$ ($N_i$ being the number of couples considered) and a second Bragg mirror having an optical pathImage available on "Original document" ($N_2$being the number of couples considered), the optical path of the flaw interposed between the first Bragg mirror and the second Bragg mirror is advantageously equal to $2n_id_i$ or to $2n_2d_2$, depending on the order of the Bragg mirrors in the sequence. The porous membrane 7 included in the device 1 according to the present invention has a number N of periods between 10 and 50, preferably between 20 and 40, still more preferably equal to 30. Advantageously, all the layers comprising the porous membrane 7 develop with a substantial parallelism with respect to the surface 8$s$ of the support element 8 on which the porous membrane 7 and/or with respect to the surface 8$p$ of the support element 8 on which the micro-needles 10 are applied.

In particular circumstances (for example if the element is deformed with consequent widening or thinning of the layers, but also, as in the present invention, if particles and/or molecules are stored in said element so they are dispersed within the layers) the wavelengths filtered by a Bragg mirror vary.

Based on the above description, the dimensioning of the porous membrane 7 starts from the definition of the desired wavelength AB. Based on the active molecules that are to be released by means of the membrane (in particular based on their dimension or molecular weight), the most suitable material for the porous membrane is selected along with the porosities PL and PH of the two layers, said porosities determining the refractive indices ni_e ΠH. The thicknesses of the layers di_e dH are then calculated, so that the sum between the optical path of the layer with low refractive index and the optical path of the layer with high refractive index is equal to mA&/2. Lastly, the number N of period is selected so as to obtain the desired optical efficiency, without thereby compromising the ease of a precise realisation of the porous membrane 7.

In an embodiment of the present invention, described purely by way of non-limiting explanation, the porous membrane 7 has the following parameters: number N of periods=30;

low refractive index ni_=1.6;
high refractive index ΠH=1.75;
porosity PL of the layer with low refractive index=68.4%;
porosity PH of the layer with high refractive index=72.6%;
thickness di_ of the layer with low refractive index di_=78 nm;
thickness dH of the layer with high refractive index dH=65 nm;
total thickness of the membrane=N(di_+dH)=4.29µıπ

When the active molecules with which the porous membrane 7 is loaded comprise molecules of at least one fluorescent substance, for example fluorescein (C20H12O5), the colour of said fluorescent substance within the porous membrane 7 depends on parameters such as the concentration of the fluorescent substance in the porous membrane 7 and/or the state of oxidation and/or of decay of the fluorescent substance in the porous membrane 7. Therefore, a veering of the colour of the fluorescent substance constitutes evidence, easily detectable even with the naked eye and/or without the aid of any instrumentation, of a variation of at least one among said parameters. In the example in which the fluorescent substance loaded in the porous membrane 7 is fluorescein, it appears to be coloured green as a result of the loading, when its concentration in the porous matrix is particularly high. Once the fluorescein is released by the porous membrane 7, it appears to be coloured green, this colour being determined by a low concentration of fluorescein in the porous matrix. If the fluorescein has remained for an excessively prolonged time in the porous membrane 7, the colour of fluorescein becomes red because of oxidation and/or decay phenomena.

Therefore, dispersing molecules of fluorescein (or of a similar fluorescent substance) in the active molecules loaded in the porous membrane 7 and then released by the device 1 through the micro-needles 10, from a simple detection of a verring in the colour (for example from green to blue) it can easily and immediately be determined that the fluorescein molecules (and with them the active molecules loaded in the porous membrane 7) were correctly released by the device 1, for example as a result of the application of the device 1 on the skin for therapeutic purposes. Moreover, by means of a simple detection of the colour of the fluorescein molecules (for example green or red), it can easily and immediately be determined whether the device 1 is effectively and/or validly usable, or if it is no longer effective, being expired and/or oxidation phenomena having occurred, which degraded the active molecules.

Use of the fluorescent substance then makes it possible, in combination with the optical properties of the porous membrane 7, to implement passive control functionalities on the device 1, based on simple chromatic observations.

Figure 3:
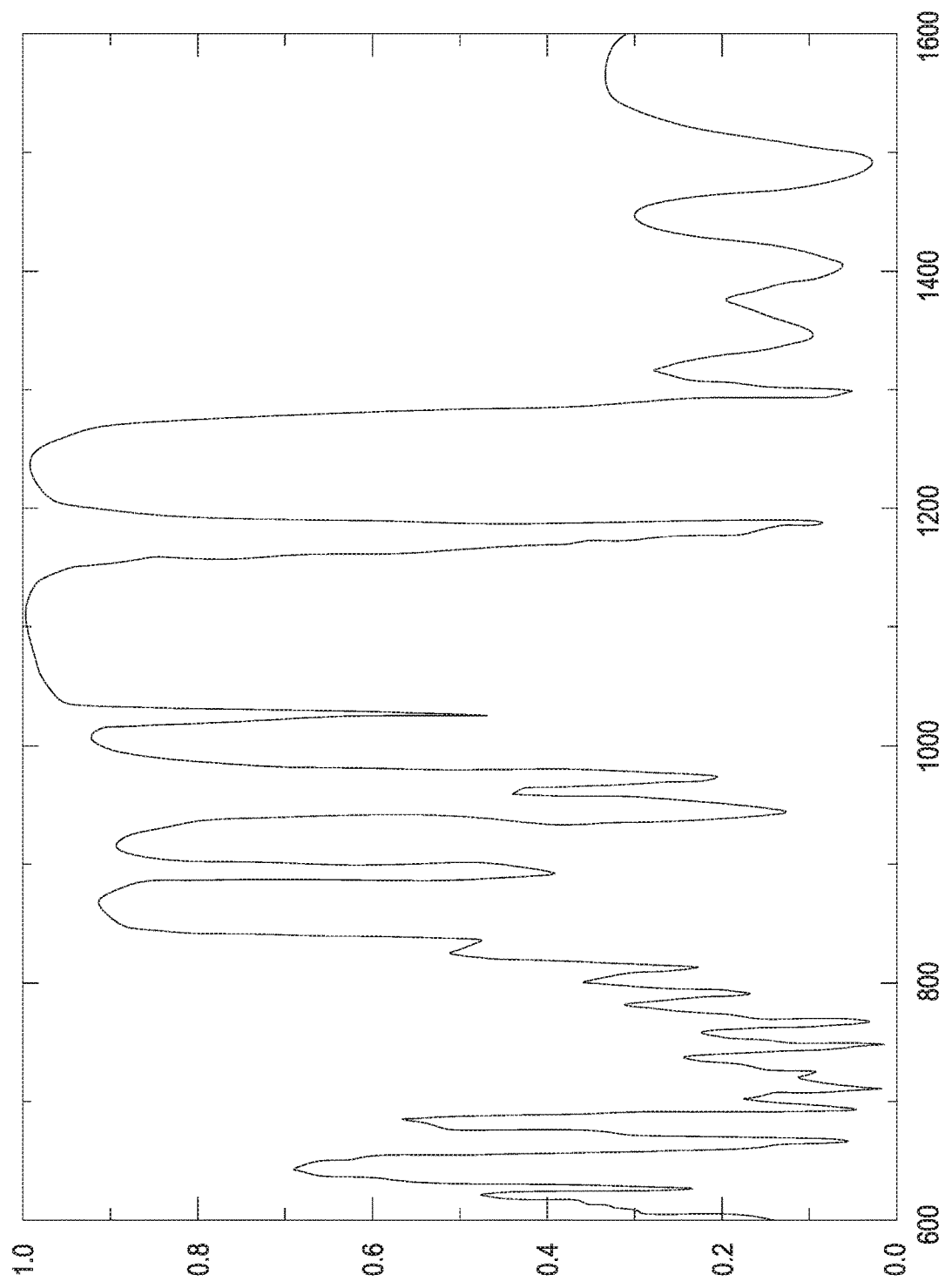
FIG. 3 represents an optical spectrum of an element of a device for the transdermal delivery of active molecules according to the present invention.

With regard instead to the contribution of the optical properties of the porous membrane 7 relative to the active control of the release of the active molecules, reference is made to FIG. 3 which represents the optical spectrum of a porous membrane 7 made of PSi. In this representation, the x-axis shows wavelength values (in nanometers), while the y-axis shows values of the reflection index (albedo). From a low reflection index corresponding with a particular value of wavelength in the optical spectrum, it is deduced that the porous membrane 7 is practically transparent if impacted by a radiation having that particular value of wavelength. From a high reflection index corresponding with a particular value of wavelength in the optical spectrum, it is deduced instead that the porous membrane 7 behaves like a mirror if impacted by a radiation having that particular value of wavelength, reflecting that radiation almost entirely. In the example of optical spectrum showed by way of non-limiting explanation in FIG. 3, it can be noted that in the near infrared spectrum there is an ample region of high reflectivity, in which however there are interruptions at transmissivity peaks due to the optical resonance of the porous membrane 7. Therefore, exposing the porous membrane 7 to a radiation having the wavelength corresponding to a trasmissivity peak, this radiation can traverse the porous membrane 7 by interferential effect.

Dispersing molecules of at least one photoresponsive substance (for example a photoresponsive polymer or hydrogel, optionally a photoresponsive derivative or ester of acrylic acid or of polyvinyl alcohol or of polymethacrylate or of hyaluronic acid or of polyethylene glycol) in the active molecules loaded in the porous membrane 7, it is possible to selectively activate the molecules of the photoresponsive substance (and with them the active molecules) exposing the porous membrane to a radiation with such wavelength that the porous membrane 7 can be traversed by the radiation by interferential effect. Therefore, coupling to the device 1 a generator of radiations having coherent wavelength and such as to allow the traversing of the porous membrane 7 (for example a laser generator configured to emit in the near infrared spectrum), it is possible to carry out the active and/or selective release of the active molecules from the porous membrane 7 and from the device 1. The peculiarity of the photoresponsive substances is that they are activated when they are exposed to light. Advantageously, polymeric mixtures can be used as photoresponsive substances. These polymeric mixtures can have variable molecular weight according to their respective uses and they can also include an active ingredient in their structure. Incidentally, it is pointed out that the optical spectrum shown by way of non-limiting explanation in FIG. 3 has an extended transmissivity region in the visible range. Therefore, the porous membrane 7, whose optical spectrum is represented in FIG. 3, in addition to the active control of the release of the active molecules, is also suitable for allowing passive control of said release. Therefore, the photosensitive substance can at first be activated by exposing the device 1 to a predetermined wavelength (in the non-visible range, for example in the near infrared) and then it can be verified that said release actually took place by means of a simple inspection of the colour of the porous membrane (colour veering from green to blue).

A further embodiment of the present invention is possible, wherein in the porous membrane 7 are dispersed molecules of a plurality of photoresponsive substances, each of which can be activated by exposure to a predetermined wavelength. In this case, the porous membrane 7 can be configured (appropriately selecting number, porosity and thickness of the layers of the porous matrix) so that the optical spectrum of said porous membrane 7 has a plurality of transmissivity windows (advantageously separate from each other) coinciding with the values of the wavelengths that activate the photoresponsive substances. The device 1 is suitable to allow not only the active release, but also the selective release of the active molecules, the wavelength to which the porous membrane 7 is exposed being selectable according to the photoresponsive substance to be released. It is then possible to define cycles of delivery through the device 1 of active molecules distinct from each other, providing the succession of exposures to radiations of different wavelength, as well as appropriate time intervals between the release of a photoresponsive substance and the release of the next photoresponsive substance.

The porous membrane 7, to obtain an active and/or selective release of the active molecules, can be used in combination with at least one thermoresponsive substance, i.e. with at least one substance capable of activating when subjected to a predetermined temperature increase for a predetermined duration. The molecules (in particular if at least one organic compound is used as a thermoresponsive substance) and/or the particles (in particular if at least one inorganic compound is used as a thermoresponsive substance) can be dispersed in the active molecules loaded in the porous membrane 7. From a physical viewpoint, the effect of the thermoresponsive substance, when headed in a controlled manner, is to change the viscosity of the porous matrix of the porous membrane 7, making possible the release through the micro-needles 10 of active molecules which otherwise would not be releasable because of the viscosity of the porous membrane 7.

As a first thermoresponsive substance substance, suitable in particular to produce temperatures up to 40° C. for a duration of up to 8 hours, a non-noble metal can be used in the form of nanoparticles, optionally iron nanoparticles, which, in the presence of oxygen and of a catalyst, optionally graphene, change oxidation state with an exothermic reaction. This second thermoresponsive substance, suitable in particular to produce rapid local temperature variations up to 3° C., gold can be used in the form of nanoparticles that are heated by irradiation and that can be obtained by reduction of a gold salt in the presence of a reducing compound, optionally sodium borohydride (the gold particles can in particular be spherical with diameter between 5 and 100 nm or cylindrical with minor axis smaller than 10 nm and major axis up to 100 nm). Since the two thermoresponsive substances produce mutually complementary effects by extent and duration of the induced heating, a simultaneous use of the two substances is extremely advantageous, inasmuch as such simultaneous use allows even complex cycles of delivery of active molecules to be defined.

In case of use of thermoresponsive molecules and/or particles, the porous membrane 7 is configured to allow the selective activation of the active molecules. In particular, if the thermoresponsive molecules and/or particles can be activated by irradiation, the optical properties of the porous membrane 7 are able to allow the porous membrane 7 to be traversed by at least one wavelength capable of realising such irradiation. The optical spectrum of the porous membrane 7 therefore has at least one transmissivity window coinciding with a wavelength suitable to allow the activation of the thermoresponsive molecules and/or particles.

In addition to an active molecule, the porous membrane 7 can be further loaded with a carrier molecule, suitable to carry the active molecule, according to a protection mechanism for protecting the active molecule to be released, which uses a sacrificial approach. The carrier molecule protects the active molecule to be released, deactivating itself and thus preserving its activity. By way of example, provided here purely by way of non-limiting explanation, a carrier suitable to be loaded in the porous membrane 7 is bovine serum albumin (BSA).

From the above it is readily apparent that in general the device 1 according to the invention, and in particular the porous membrane 7, have distinctive features both in terms of morphology, and of surface chemistry, which allow to modulate the release of the active molecules over time. The release can take place according to predetermined time intervals, for example by means of programmed exposures, appropriately distanced from each other in terms of time. The release can further take place in a targeted manner, for example distriminating the active molecules according to their hydrophobic and/or hydrophilic nature. For this purpose, it is pointed out that, by virtue of the structure of the device 1, electronic control devices (which may be integrated) can be connected thereto, such as microcontrollers, as well as sensors and/or transducers and/or actuators, also realised exploiting nanotechnologies. From the above it is also readily apparent that the device 1 as described above is suited for a wide range of uses (both within the pharmaceutical field, and within the cosmetics field), of which some of the most peculiar are listed below: i) INVENTIVE USE OF THE DEVICE FOR MONITORING THE RELEASE AND/OR THE DECAY OF THE ACTIVE MOLECULES:

since the porous membrane 7 (which, it should be recalled, is configured to behave, from an optical viewpoint, as a Bragg mirror or as a linear combination between Bragg mirrors or as a single or coupled optical cavity, specifically because of the porous matrix made of PSi) was loaded with active molecules comprising molecules of at least one fluorescent substance, in particular fluorescein (C20H12O5), the release and/or any decay of the active molecules can easily be monitored (by the person who wears the device 1, as well as by medical and/or paramedic personnel) by means of immediate chromatic observations. The device 1 can be configured so that the colour of the fluorescent substance veers as a result of a change of the concentration of the active molecules and/or or the fluorescent substance in the porous membrane 7. If fluorescein is used, a green colour is visually observed before the release of the active molecules through the micro-needles 10, said colour indicating a high concentration of fluorescein in the porous matrix. A blue colour is instead visually observed as a result of the release of the active molecules through the micro-needles 10, said colour indicating a high concentration of fluorescein in the porous matrix. Once the device 1 is applied on the skin, polymeric diffusion phenomena are triggered so that the active molecules tend to be move from the micro-needles 10 to the biological fluids and at the same time from the porous membrane 7 to the micro-needles 10 (these phenomena have been observed, inter alia, in laboratory tests, in which, to simulate the move towards the biological fluids, the device 1 was immersed in a phosphate-buffered saline and which showed that, in a time interval of 8 hours, approximately 70% of the active molecules are released from the device 1). Alternatively or advantageously in addition to the visual monitoring of the release, the device 1 can be configured so that the colour of the fluorescent substance veers as a result of a change of the state of oxidation and/or of decay of the active molecules and/or of the fluorescent substance in the porous membrane 7. If fluorescein is used, a green colour is visually observed when the porous membrane 7 upon charging the active molecules, said colour indicating full effectiveness of the active molecules. Instead, a red colour is visually observed as a result of the degradation of the active molecules, through said colour the person subjected to therapeutic treatment being informed that the device 1 is expired or otherwise unusable. The device 1 of the present invention can also be used as a means for the controlled release of active molecules in the treatment of different types of pathologies, including the sub-cutaneous release of drugs in the field of oncology. For some types of active molecules to be released, the procedure for fabricating the device 1 and/or for charging the device 1 with active molecules can have an effect on the activity of the molecules. A mechanism for the protection of the active molecule to be released through a sacrificial approach can also be adopted. According to this approach, a second molecule, for example a protein, is used as the carrier molecule of the active molecule to be released. The carrier molecule serves the function of protecting the active molecule to be released, deactivating itself and thus preserving its activity. A carrier suitable for being used in the aforesaid sacrificial approach is bovine serum albumin (BSA), since it is suitable for being employed in association with active molecules of different types. The BSA, by way of example provided herein purely by way of non-limiting explanation, is suitable for being employed in the control of "wound healincf" mechanisms (treatment of cutaneous lesions). If in the porous membrane 7 are defined coupled optical cavities and it is thus possible to use the porous membrane 7 for the release of more than one active ingredient, for the monitoring of the release and/or of the decay of the active molecules, a variation can be appropriately provided between a plurality of colours, corresponding for example to the conditions in which no active ingredient has been released, in which only a first active ingredient has been released, in which only a second active ingredient has been released, in which only a specific combination of active ingredients has been released and in which all active ingredients have been released; INVENTIVE USE OF THE DEVICE FOR THE OPTICAL CONTROL OF THE RELEASE OF THE ACTIVE MOLECULES:

the porous membrane 7 (which, it should be recalled, is configured to behave, from an optical viewpoint, as a Bragg mirror as a linear combination between Bragg mirrors or as a single or coupled optical cavity, specifically because of the porous membrane made of PSi) having been loaded with active molecules comprising molecules of at least one photoresponsive substance (a photoresponsive polymer or a photoresponsive hydrogel, able to be activated when exposed to particular electromagnetic radiations), the optical spectrum of the porous membrane 7 can be exploited to activated in a controlled manner the photoresponsive substance loaded in the porous membrane 7, so as to make the release of the active molecules become a selective release. The activation of the photoresponsive substance and the consequence release of the active active molecules through the micro-needles 10, in fact, occur only upon the occurrence of a predetermined condition, said predetermined condition being the exposure of the device 1 to a radiation having a wavelength coinciding with which the optical spectrum of the porous membrane 7 has a transmissivity window or which is included in a transmissivity window of the optical spectrum of the porous membrane 7. Advantageously, the exposure to which the release of the active molecules from the device 1 is subordinated is an exposure to a radiation whose wavelength is not positioned in the visible range. For example, the transmissivity window of the porous membrane 7 and correspondingly the wavelength of activation of the photoresponsive substance can be positioned in the infrared range, in particular in the near infrared range. Therefore, by means of a system for the release of active molecules comprising the device 1 and a radiation generator (which acts as a source of radiations having such wavelength as to be able to traverse the porous membrane 7 by interferential effect and which can be integrated in the device 1 or constitute a stand-alone device), both the quantity of molecules released, and the time in which said release is carried out, can be determined. Since the radiation generator is typically a programmable electronic device, it is possible to define programmes for the automatic release of the active molecules from the device 1, implementable by means of the radiation generator. If coupled optical cavities are defined in the porous membrane 7 and it is thus possible to use the porous membrane 7 for the release of more than one active ingredient, it is possible, for the optical control of the release of the active molecules, to load in the porous membrane 7 molecules of drugs that are photoactivatable through exposure to different wavelengths and to advantageously define programmes for automatic release which regulate, inter alia, the succession whereby the photoactivatable drugs are released, as well as the time interval between the various releases. In case of coupled cavities that behave, from an optical viewpoint, as a combination between Bragg mirrors, the porous membrane 7 can be configured (appropriately selecting number, porosity and thickness of the layers of the porous matrix) so that the optical spectrum of said porous membrane 7 has a plurality of transmissivity windows (advantageously separate from each other) coinciding with the values of the wavelengths that activate the photoresponsive substances. The device 1 is suitable to allow not only the active release, but also the selective release of the active molecules, the wavelength to which the porous membrane 7 is exposed being selectable according to the photoresponsive substance to be released. It is then possible to define cycles of delivery through the device 1 of active molecules distinct from each other, providing the succession of exposures to radiations of different wavelength, as well as appropriate time intervals between the release of a photoresponsive substance and the release of the next photoresponsive substance; iii) INVENTIVE USE OF THE DEVICE FOR THE THERMAL CONTROL OF THE RELEASE OF THE ACTIVE MOLECULES:

the porous membrane 7 having been loaded with active molecules comprising molecules and/or particles of at least one thermoresponsive substance (for example nanoparticles of a non-noble metal, in combination with a catalyst, and/or gold nanoparticles), the ability of said thermoresponsive substance to activate when subjected to a predetermined increase in temperature for a predetermined duration can be exploited to make the release of the active molecules selective. The activation of the thermoresponsive substance, and consequently the release of the active molecules through the micro-needles 10, take place only upon the occurrence of a predetermined condition, said predetermined condition being the exposure of the device 1 to a heat source and/or to a radiation (advantageously in the infrared range) able to activate the thermoresponsive substance. Said exposure is able to activate the active molecules causing an (exothermic) oxidation reaction or supplying heat that is absorbed by irradiation. Combining thermoresponsive substances with different activation characteristics, it is advantageously possible to define programmes for the selective release of the active molecules, in which the specificity of each thermoresponsive substance is exploited to obtain an optimal release of the active molecules. These programmes can be implemented by heating means and/or by radiation generators that operate in combination with the device 1 (standalone or integrated in the device 1) and that can be electronically controlled. In an embodiment, in the use of the device 1, through an appropriate activation of the thermoresponsive substance stored in mutual combination in the porous membrane 7, a slow, gradual release of the active molecules is combined (said mode being in particular obtained by activating the particles comprising non-noble metals) with an intense and punctual release of the active molecules (said mode being in particular obtained by activating the particles comprising gold).

An object of the present invention, in addition to the device 1 for the transdermal delivery of active molecules and to the uses of the device 1, also methods for producing the device 1 and its components.

A first method according to the present invention is represented in the figures from FIG. 1*a* to FIG. 1*f* and it pertains to the production of a component 1 *p* usable in the device 10 for the transdermal delivery of active molecules. This component 1 *p* integrates in particular in a single body the support element 8 and a plurality of micro-needles 10 that protrude from a surface 8*p* of the support element 8 on the basis of a predetermined arrangement. Characteristically, the method for producing the component 1 *p* comprises the step of obtaining the micro-needles 10 on the surface 8*p* of the support element 8 with photolithographic or micromechanical techniques. FIG. 1*a* shows how the support element 8 is obtained by photolithography. A measured quantity of a photoresistant solution (for example 1 ml) is poured on a substrate 5 made of a material that is transparent to UV radiations (i.e. to radiations in the ultraviolet range). Quartz can be used as the constituent material for the substrate 5, while a photoresistant hybrid polymeric mixture can be used for the photoresistant solution, for example a photoresistant mixture based on PolyEthylene (Glycol) DiAcrylate (PEGDA) and on a photocatalyst, optionally 2-Hydroxy-2-methyl-1-phenyl-propan-1-one (Darocur®), said photoresistant mixture advantageously having a concentration of 2-Hydroxy-2-methyl-1-phenyl-propan-1-one (Darocur®) in PolyEthylene (Glycol) DiAcrylate (PEGDA) of approximately 2% volume/volume. Since the mixture of Darocur® in PEGDA has the behaviour of a negative photoresistive solution, it ramifies if exposed to a UV source. The photoresistant mixture is therefore hardened by exposure to UV radiations (represented graphically by parallel arrows). A possible exposure time is equal to 10 s, at the end of which the support element 8 with a thickness of approximately 1 mm is obtained, the support element 8 remaining attached to the substrate 5 so as to form a block.

Figure 1B:
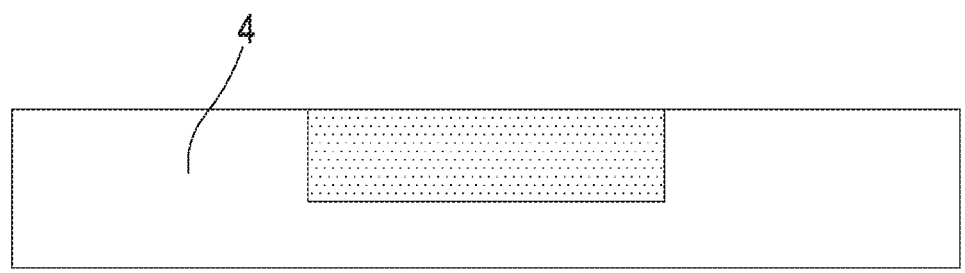

FIG. 1*b* shows a preparatory step, in which a container 4 (whose capacity may be 1.41 mL, obtained with the dimensioning of 16 mm×20 mm×4.4 mm), preferably made of silicone, if filled to its edges with a photoresistant mixture. The photoresistant mixture with which the container is filled is advantageously the same photoresistant mixture used as the starting material for the realisation of the support element 8, hence a photoresistant mixture based on PolyEthylene (Glycol) DiAcrylate (PEGDA) and with a photocatalyst, optionally 2-Hydroxy-2-methyl-1-phenyl-propan-1-one (Darocur®), in particular said photoresistant mixture having a concentration of 2-Hydroxy-2-methyl-1-phenyl-propan-1-one (Darocur®) in PolyEthylene (Glycol) DiAcrylate (PEGDA) of approximately 2% volume/volume.

Figure 1C:
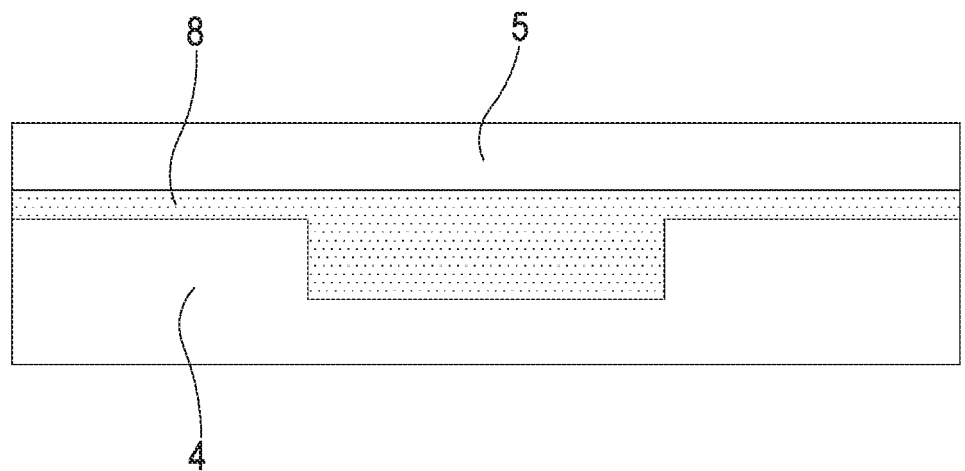

FIG. 1*c* shows that the block consisting of the support element 9 and of the substrate 5, after being overturned, bears on the edges of the container 4 so as to close the container 4 and to be in direct contact with the photoresistant mixture contained in the container 4.

Figure 1D:
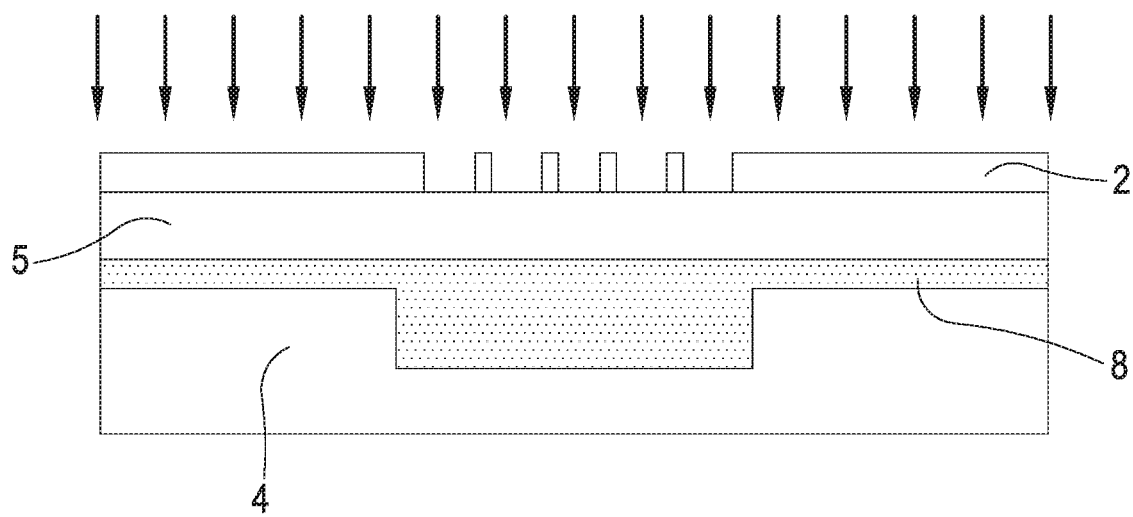

FIG. 1*d* shows the exposure to the UV source directed at forming, by photolithography, of the micro-needles 10 on the surface 8*p* of the support element 8, starting from the photoresistant mixture contained in the container 4. For this purpose, a mask 2 made of a material that is impermeable to UV ratiation (for example quarts/chromium) bears on the substrate 5, so as to be interposed between the photoresistant mixture to be hardened and a UV source. On the mask 2 have been obtained openings at the points on which the micro-needles 10 that will be formed on the support element 8 are to be positioned. A time of exposure to the UV source that is particularly suited for forming the micro-needles 10 is 7.5 s.

Figure 1E:
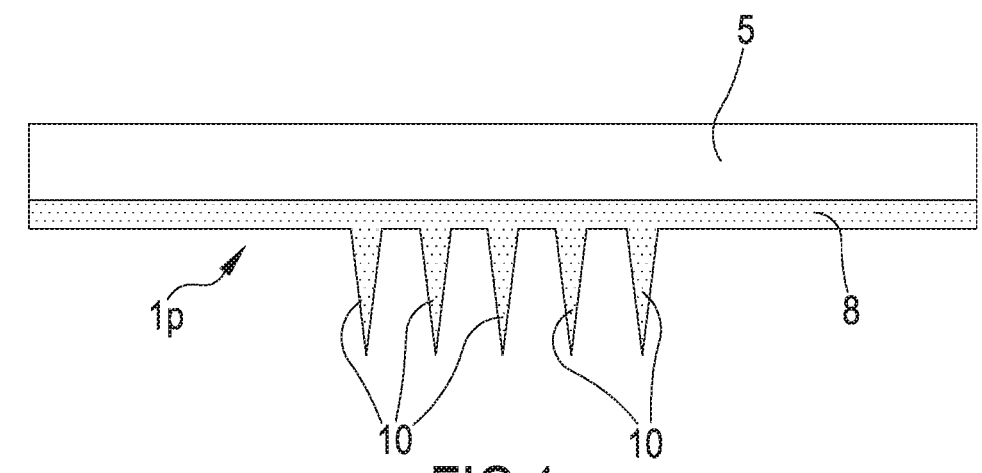

FIG. 1*e* shows the definition of the micro-needles 10, once photolithography is completed. The micro-needles 10 are first subjected to a step of washing in deionized water for approximately 2 minutes, to remove the unhardened photoresistant mixture, and then to a step of drying with nitrogen.

Figure 1F:
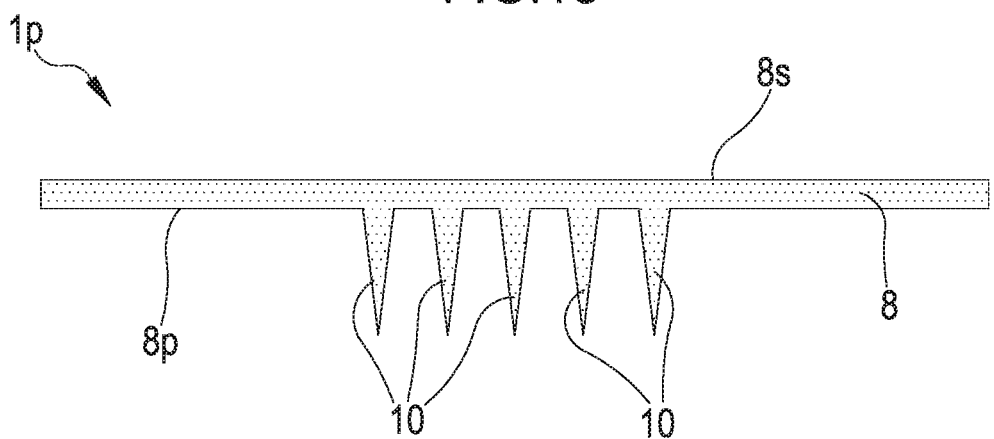

Lastly, FIG. 1*f* shows the removal, by cutting, of the substrate 5. The component 1 *p* of polymeric material was thus definitively obtained, said component 1 *b* being a single body that integrates the support element 8 and the microneedles 10. A second method according to the present invention pertains to the production of a porous membrane 7 usable in the device 10 for the transdermal delivery of active molecules. Characteristically, the method for producing a porous membrane 7 comprises the step of configuring the porous membrane 7 to behave, from an optical viewpoint, as a Bragg mirror or as a linear combination between Bragg mirrors or as a single or coupled optical cavity. For the production of the porous membrane 7 with the optical characteristics of a Bragg mirror, a porous membrane having high specific surface area with resonant photonic structure is realised, the realisation of the porous membrane entailing the superposition of layers with different porosity, in which a layer with lower porosity is alternated to a layer with higher porosity. Advantageously, wanting to obtain a porous membrane 7 with a number N of periods between 10 and 50, preferably between 20 and 40, still more preferably equal to 30, between 10 and 50, preferably between 20 and 40, still more preferably 30 layers with lower porosity are realised, alternating them to the same number of layers with greater porosity.

A particularly suitable material for the realisation of the porous membrane 7 is porous silicon (PSi). It is stressed that this material is adequate not only to give the desired optical characteristics to the porous membrane 7, but also to make it self-supporting. In an embodiment of the method for producing the porous membrane 7 according to the present invention, the porous membrane 7 is obtained by an electrochemical process. For example, the porous membrane 7 can be obtained by electrochemical dissolution of crystalline silicon with p++ doping in a solution of hydrofluoric acid (HF), water and ethanol, hydrofluoric acid (HF), water and ethanol being in a ratio of approximately 1:1:1 in this solution. The etching is carried out in conditions of darkness and at ambient temperature. Crystalline silicon, preliminarily to the electrochemical process, is advantageously subjected to a treatment able to remove oxides from its surface, said treatment being able to be carried out by immersion of the crystalline silicon for approximately 2 minutes in a solution of hydrofluoric acid (HF).

The layers constituting the porous membrane 7 are dissolved one by one, providing a pause of approximately 5 s between one dissolution and the next one, to recover the correct concentration of hydrofluoric acid (HF) in the electrochemical bath. The current density used to dissolve the layers with higher porosity is approximately twice the current density used to dissolve the layers with lower porosity.

Once the etching of all layers is completed, a high current density is applied to separate the porous membrane 7 from the crystalline silicon left undissolved. Once the porous membrane 7 is realised, it is advantageously subjected to an oxidation treatment (which can consist of immersing the porous membrane 7 in an ethanol solution at ambient temperature for a time interval of approximately 24 hour) and then allowed to dry at ambient temperature. The porous membrane 7 thus obtained is suitable to be used in the device 1 and therefore to be loaded with active molecules (possibly also with one or more fluorescent and/or photoresponsive and/or thermoresponsive substances).

The electrochemical dissolution process described above makes it possible, advantageously, to effect an intrinsic modulation of the porosity of the porous membrane 7, to obtain an adaptation of the porous membrane 7 to the molecular dimension of the active ingredient to be released. The parameters of the electrochemical dissolution process that can be varied for the purposes of said intrinsic modulation are: the doping of the crystalline silicon, on which substantially depends the shape of the pores and/or the concentration of the hydrofluoric acid (HF), on which depends the size of the pores, the desired size of the pores being a function of the size of the molecules of the active ingredient to be released (in particular, the size of the pores can vary from 1 nm to 10 micron) and/or the current density in the electrochemical cell where the electrochemical dissolution process takes place, on which depends the porosity of the porous membrane 7 (in particular, the porosity of the porous membrane 7 can vary between 30% and 80%, and it can reach up to 85%, and further up to 90%, adopting special procedures such as drying the porous membrane 7 with supercritical $CO_2$) and/or the time of electrochemical etching, on which the thickness of the porous membrane 7 depends (in particular, the thickness of the porous membrane 7 can vary from 1 micron to 500 micron).

It is therefore possible to vary the morphological properties of the porous membrane 7, when it is based on porous silicon (PSi), in order to modulate the quantity of active ingredient loaded therein (from a few microgrammes to tens of milligrammes per cm$<2>$) and/or to modulate the rate of release of the active ingredient, being able thereby to obtain a massive release of the active ingredient (relatively large quantities of active ingredient released in a relatively short time) or a slow release of the active ingredient (relatively small quantities of active ingredient released in a relatively long time).

Within the second method according to the present invention it is also possible to obtain an intrinsic modulation of the chemical nature (in particular of the surface chemistry) of the porous membrane 7, for the purposes of an adaptation thereof to the hydrophobic or hydrophilic behaviour of the active ingredient to be released. It should be recalled that the behaviour of an active ingredient is called "hydrophobic" (or alternatively "lipophilic") when the molecules that comprise said active ingredient do not dissolve in water, when the behaviour of an active ingredient is called "hydrophilic" when the molecules that comprise said active ingredient dissolve in water.

The quantity and the time of release of the molecules of active ingredient depend not only on the morphology of the porous membrane 7, but also and above all on its chemical nature, which determines its hydrophobic or hydrophilic behaviour. In particular, porous silicon as just produced is hydrophobic (the angle of contact with water being approximately 130°). The wettability of porous silicon can thus be modified through thermal passivation techniques (transforming it partially or completely into porous, highly hydrophilic S1O2) or chemical passivation techniques (covalently bonding to the surface compounds that have hydrophilic terminations, for example APTES and APMDES siloxanes, or infiltrating the membrane with amphiphilic polymers). Following passivation (be it thermal or chemical), the optical properties of the porous membrane are altered. For example, silicon has refractive index above 4 (in the visible spectrum), while silicon dioxide (S1O2) has refractive index between 1.4 and 1.6 and the refractive index of porous silicon (PSi) can be lower than 1.2. Therefore, if the porous membrane 7 has to be subjected to specific treatments after electrochemical dissolution (for example to a passivation treatment), account can advantageously be taken, by means of appropriate algorithms, of the effect of such treatments on the optical properties of the porous membrane 7 and therefore to modulate the entire process (electrochemical dissolution and subsequent thermal or chemical passivation), so that, at the end, the desired optical properties are obtained.

Lastly, it is stressed that, modulating the chemical nature (in particular the surface chemistry) of the porous membrane 7 (and consequently varying the interaction between the active ingredient and the surface of the porous membrane 7), it is possible to determine not only the quantity of molecules of active ingredient that can be loaded inside the porous membrane 7, but also their physical state (liquid or crystalline) because, due to the pressure in the nanopores of the porous membrane 7, the molecules of active ingredient in solid form can liquefy.

A third method according to the present invention is represented in the figures from FIG. 2a to FIG. 2d and it pertains to the production of the device 10 for the transdermal delivery of active molecules. The third method employs both the first method, and the second method described previously: characteristically, in said third method, the component 1 $p$ obtained by means of the aforesaid first method is assembled with the porous membrane 7 obtained by means of the aforesaid second method.

FIG. 2a shows the depositing of the porous membrane 7 on a closing element 9, said closing element 9 being realisable from a photoresist hybrid polymeric mixture (for example from photoresistant mixture based on PEGDA and on a photocatalyst, optionally Darocur®, in particular said photoresistant mixture having a concentration of Darocur® in PEGDA of approximately 2% volume/volume) or of quartz and advantageously having a substantial shape identity with the component 1 $p$, in particular with the support element 8. The closing element 9 can advantageously be obtained through a similar process to the one used for producing the support element 8 (i.e. hardening by exposing to UV radiation a photoresistant mixture deposited on a substrate that is then removed by cutting). Once it is placed on the closing element 9, the porous membrane 7, if wet, is allowed to dry.

FIG. 2b shows the loading of the porous membrane 7 with the active molecules. Loading can take place by means of a dispenser able to release the substance with the active molecules drop by drop. Depending on the future use of the device 1 and/or of the functionalities to be provided to the device 1, the active molecules that are stored in the porous membrane 7 can comprise molecules of at least one fluorescent substance, in particular fluorescein ($C_{20}H_{12}O_5$), and/or molecules of at least one photoresponsive substance, in particular a photoresponsive polymer or hydrogel, optionally a photoresponsive derivative or ester of acrylic acid or of polyvinyl alcohol or of polymethacrylate or of hyaluronic acid or of polyethylene glycol and/or molecules and/or particles of at least one thermoresponsive substance, said thermoresponsive substance comprising in particular nanoparticles of a non-noble metal, optionally iron, and a catalyst, optionally graphene, and/or gold nanoparticles. The total loading of the porous membrane 7 can be of the order of 0.05 ml or greater. If the device 1 of the present invention is configured to be employed using the sacrificial approach, according to which an active molecule is carried by a carrier module (for example BSA) which preserves its activity, the loading step of FIG. 2b contemplates loading both the active molecule and the carrier module in the porous membrane.

FIG. 2c shows the assembly of the device 1. On the surface of the covering element 9 on which the porous membrane 7 is positioned, a photoresistant liquid is peripherally applied, as represented schematically in the figure by local application positioned in proximity to the corners. The photoresistant liquid is advantageously a hybrid photoresistant mixture, for example a photoresistant mixture based on PEGDA and a photocatalyst, optionally Darocur®, in particular said photoresistant mixture having a concentration of Darocur® in PEGDA of approximately 2% volume/volume. At this point, the component 1p is positioned on the covering element 9, placing the surface 8s of the support element 8 in contact with the surface of the covering element 9 on which bears the porous membrane 7 (which thus remains interposed between the component 1 p and the covering element 9).

Lastly, FIG. 2d shows the connection of the component 1 p to the covering element 9. Said connection is achieved by hardening, through exposure to a UV source, the photoresistant liquid previously applied between the covering element and the component 1 p. At the end of the exposure, the porous membrane 7 remains adequately sealed inside the device 1. Use of the photoresistant liquid for the connection between the covering element 9 and the component 1 p is extremely advantageous, both for the reliability of the connection thus obtained, and for its rapidity, an exposure of 10 s being sufficient to harden the photoresistant mixture. Alternatively, it is in any case possible to connect together the covering element 9 and the component 1 p through the application of a glue, which is also suitable to assure that the porous membrane 7 remains adequately sealed. From the detailed description of the invention, it can be appreciated that it is fully suited to achieve all the purposes for which it was conceived. The device 1 according to the present invention assures optimal delivery of the active molecules and can be beneficially used in combination with active molecules both in pharmaceutics and in cosmetics. The device 1 is distinguished by its versatility not only because it lends itself to multiple applications, but also because the method for its realisation makes it easy to make changes in the structure and/or in the dimensions and/or in the materials of the device 1. Moreover, the device 1, making possible both passive control, and active control of the release of the active molecules, is very effective, reliable and comfortable both when used for therapeutic purposes, and when used for diagnostic purposes.

The presence of the micro-needles 10 assures that the active molecule will overcome the resistance provided by the corneal layer of the skin and reach the interstitial liquid. Moreover, the potential provided to the device 1 by the active control of the release of the active molecules allow to deliver said active molecules according to the best dosage and delivery time. Lastly, the potential provided to the device 1 by monitoring the release of the active molecules enable the person wearing the device 1 to have available an interface (in the form of a colour) that is very easy to interpret and that can be consulted immediately

What is claimed is:

1. A device for the transdermal delivery of active molecules comprising:
    a support element permeable to said active molecules;
    a plurality of micro-needles permeable to said active molecules, said micro-needles protruding from a first surface of said support element and
    a porous membrane configured to be loaded with said active molecules, said porous membrane lying on a second surface of said support element;
    wherein said porous membrane is configured to be an optical Bragg mirror or a linear combination between optical Bragg mirrors or at least one single or coupled optical cavity, said optical Bragg mirror or said optical Bragg mirrors in said linear combination or said at least one single or coupled optical cavity having a periodic structure with the alternation of layers with low refractive index and layers with high refractive index,
    the number of periods in said porous membrane being between 10 and 50.

2. The device according to claim 1, wherein said second surface is the surface of said support element opposite to said first surface.

3. The device according to claim 1, wherein said micro-needles and said support element are a single body.

4. The device according to claim 1, wherein said micro-needles and/or said support element comprise a photoresistant hybrid polymeric mixture.

5. The device according to claim 4, wherein said photoresistant hybrid polymeric mixture is a photoresistant mixture based on Poly Ethylene DiAcrylate and on a photocatalyst.

6. The device according to claim 5, wherein said photoresistant mixture has a concentration of 2-Hydroxy-2-methyl-1-phenyl-propan-1-one in PolyEthylene DiAcrylate of 2% volume/volume.

7. The device according to claim 1, wherein said micro-needles extend from a first portion of said support element and said porous membrane contacts a second portion of said support element, wherein said first portion is internal to said second portion, said active molecules diffusing from said porous membrane in said support element and thence in said micro-needles.

8. The device according to claim 1, wherein a closing element is connected to said second surface of said support element, said closing element adhering peripherally to said support element, said porous membrane being sealed between said closing element and said support element, said closing element being made of the same material as said support element and/or based on at least one photoresistant hybrid polymeric mixture.

9. The device according to claim 8, wherein an extension of said micro-needles is between 0.1 mm and 2 mm, and/or wherein a thickness of said support element is between 0.3 and 1.8 mm, a thickness of said closing element being between 0.2 mm and 1.2 mm.

10. The device according to claim 1, wherein said porous membrane comprises a porous matrix having a surface area with resonant photonic structure, said porous membrane comprising layers with different porosity.

11. The device according to claim 1, wherein said porous membrane is configured to be further loaded with carrier molecules, said carrier molecules being suitable to carry said active molecules.

12. The device according to claim 1, wherein said active molecules comprise molecules of at least one fluorescent substance, a colour of said fluorescent substance veering as a result of a change of at least one representative parameter of said fluorescent substance in said porous membrane, wherein said porous membrane is configured to have at least one transmissivity window in a spectrum of visible light, said transmissivity window including the range of wavelengths of a radiation emitted by said fluorescent substance when said at least one parameter is within a predefined range.

13. The device according to claim 12, wherein said parameter comprises a concentration of said fluorescent substance in said porous membrane and/or a state of oxidation and/or of decay of said fluorescent substance in said porous membrane, wherein said porous membrane is configured to have:
   at least a first transmissivity window in the spectrum of visible light, said first transmissivity window including a range of wavelengths of the radiation emitted by said fluorescent substance when the concentration of said fluorescent substance in said porous membrane is a result of a charging of said fluorescent substance in said porous membrane and/or
   at least a second transmissivity window in the spectrum of visible light, said second transmissivity window including the range of wavelengths of the radiation emitted by said fluorescent substance when the concentration of said fluorescent substance in said porous membrane is a result of the release of said fluorescent substance by said porous membrane and/or
   at least a third transmissivity window in the spectrum of visible light, said third transmissivity window including the range of wavelengths of the radiation emitted by said fluorescent substance when said fluorescent substance in said porous membrane is decayed, as a result of the state of oxidation over time of said fluorescent substance in said porous membrane.

14. The device according to claim 13, wherein said at least first transmissivity window and/or said at least second transmissivity window and/or said at least third transmissivity window are further configured to be transmissivity windows in an infrared spectrum.

15. The device according to claim 1, wherein said active molecules comprise molecules of at least one photoresponsive substance, wherein said porous membrane is configured to have at least one transmissivity window and to allow a radiation to which said porous membrane is exposed to traverse said porous membrane only if the wavelength of said radiation coincides with said transmissivity window or is included in said transmissivity window.

16. The device according to claim 15, wherein said photoresponsive substance comprises a photoresponsive polymer or hydrogel.

17. The device according to claim 1, wherein said active molecules comprise molecules and/or particles of at least one thermoresponsive substance, said thermoresponsive substance configured to active when subjected to a temperature increase for a predetermined duration.

18. The device according to claim 17, wherein said active molecules comprise molecules and/or particles of a first thermoresponsive substance and molecules and/or particles of a second thermoresponsive substance, said first thermoresponsive substance comprising nanoparticles of a non-noble metal, which in the presence of oxygen and of a catalyst is configured to change oxidation state with an exothermic reaction, said second thermoresponsive substance comprising gold nanoparticles obtained by reduction of a gold salt in the presence of a reducing compound, said gold nanoparticles being spherical with a diameter between 5 and 100 nm or cylindrical with a minor axis smaller than 10 nm and a major axis up to 100 nm.

* * * * *